United States Patent [19]

Martan

[11] 4,049,733

[45] Sept. 20, 1977

[54] SYNTHESIS OF DIPHENYLMETHANE USING PHOSPHORIC-SULFURIC ACID CATALYST

[75] Inventor: Michael Martan, Skokie, Ill.

[73] Assignee: UOP Inc., Des Plaines, Ill.

[21] Appl. No.: 623,230

[22] Filed: Oct. 17, 1975

[51] Int. Cl.$^2$ ............................................. C07C 15/16
[52] U.S. Cl. ............................ 260/668 C; 260/668 R
[58] Field of Search ..................... 260/668 C, 668 R

[56] References Cited

U.S. PATENT DOCUMENTS

| | | | |
|---|---|---|---|
| 2,526,896 | 10/1950 | Ipatieff et al. | 260/668 R |
| 2,557,505 | 6/1951 | Ipatieff et al. | 260/668 R |
| 2,671,815 | 3/1954 | Pines et al. | 260/668 R |
| 3,714,280 | 1/1973 | Stapp | 260/668 C |
| 3,799,991 | 3/1974 | Smith | 260/668 R X |
| 3,833,677 | 9/1974 | Grard | 260/668 R |
| 3,888,937 | 6/1975 | Siskin et al. | 260/667 |

FOREIGN PATENT DOCUMENTS

| | | | |
|---|---|---|---|
| 668,283 | 3/1952 | United Kingdom | 260/668 C |
| 274,098 | 9/1970 | U.S.S.R. | 260/668 C |

OTHER PUBLICATIONS

O'Conner et al., J. Amer. Chem. Soc. 60, 125 (1938).
Monacelli et al., J. Amer. Chem. Soc. 63, 1722 (1941).
Simons et al., J. Amer. Chem. Soc. 62, 1623 (1940).
Tronov et al., Bull. Gen. Chem. USSR 23, 1067 (1953).
Samsonova et al., CA 68:86964f (1968).
Nenitzescu et al., CA 52:309i (1958).
Topchiev et al., CA 45:3825d (1951).
Baddeley et al., CA 50:261e (1956).

Primary Examiner—Daniel E. Wyman
Assistant Examiner—Thomas A. Waltz
Attorney, Agent, or Firm—James R. Hoatson, Jr.; Raymond H. Nelson; William H. Page, II

[57] ABSTRACT

Diphenylmethane may be synthesized in relatively higher yields than has hereinbefore been obtained by reacting dibenzyl ether with benzene in the presence of protonic acid catalysts which contain a phosphoric acid.

5 Claims, No Drawings

SYNTHESIS OF DIPHENYLMETHANE USING PHOSPHORIC-SULFURIC ACID CATALYST

BACKGROUND OF THE INVENTION

Heretofore, one of the known methods for the synthesis of diphenylmethane is the benzylation of benzene with benzyl chloride or benzyl alcohol. Another method of obtaining the desired product is to utilize dibenzyl ether, which is a byproduct in the large scale operation by which benzyl chloride is hydrolyzed to form benzyl alcohol, and reacting the aforesaid dibenzyl ether with benzene in the presence of boron trifluoride as the catalytic agent. However, the yields which are obtained when using this particular reaction are reported to be in the range of from 20-46%. Another drawback which is encountered when utilizing this process is that the catalyst is not readily recoverable due to the formation of water during the reaction. It has also been reported that higher yields may be obtained by the benzylation of benzene with dibenzyl ether using hydrogen fluoride or aluminum chloride as the catalyst. The disadvantage which is encountered when using these catalysts is that the molar ratio of dibenzyl ether to benzene was greater than 16:1. This high molar ratio therefore makes this process expensive to operate in a batch scale operation thereby increasing the cost of the desired product.

In contradistinction to these processes, I have now discovered that, by utilizing certain catalytic compositions of matter, and particularly when using a protonic acid catalyst, one component of which is a phosphoric acid, it is possible to obtain diphenylmethane when reacting dibenzyl ether with benzene in a relatively high yield with a selectivity to diphenylmethane of greater than 90%.

This invention relates to a process for obtaining diphenylmethane. More specifically, the invention is concerned with an improved process for obtaining higher yields of diphenylmethane with a greater selectivity to the desired product when reacting dibenzyl ether with benzene in the presence of certain catalytic compositions of matter.

Diphenylmethane is a valuable product in the chemical industry. For example, the compound which is also known as benzylbenzene is used in organic syntheses, in dyes and in the perfume industry. In addition, the compound is also an intermediate which is used in the synthesis of benzophenone. The latter compound is also a valuable compound in the chemical industry, being used in organic syntheses, in perfumery, especially for floral odors, as a fixitive, or as an ultra-violet sensitizer for photopolymerization, while derivatives of benzophenone are used as ultra-voilet absorbers.

It is therefore an object of this invention to provide a process for the preparation of diphenylmethane.

A further object of this invention is to provide a process for obtaining diphenylmethane in a process whereby greater selectivity of the desired product may be obtained when reacting dibenzyl ether with benzene.

In one aspect an embodiment of this invention resides in a process for the preparation of diphenylmethane which comprises reacting dibenzyl ether with benzene in the presence of a protonic acid catalyst containing a phosphoric acid at reaction conditions, and recovering the resultant diphenylmethane.

A specific embodiment of this invention is found in a process for the preparation of diphenylmethane which comprises reacting dibenzyl ether with benzene in the presence of a protonic acid catalyst comprising polyphosphoric acid at a temperature in the range of from about 50° to about 250° C. and a pressure in the range of from about atmospheric to about 100 atmospheres, and recovering the resultant diphenylmethane.

Other objects and embodiments will be found in the following further detailed description of the present invention.

As hereinbefore set forth the present invention is concerned with an improvement in the process for the synthesis of diphenylmethane whereby greater yields of a higher selectivity to the desired product may be obtained. The synthesis of the diphenylmethane is effected by reacting benzene with dibenzyl ether in the presence of certain catalytic compositions of matter. The catalysts which are used to obtain a greater yield of the desired product comprise protonic acid catalyst systems containing a phosphoric acid. The protonic acid catalyst system may contain only a phosphoric acid or the phosphoric acid may be admixed with other protonic acids such as sulfuric acid or with a Friedel-Crafts type metal halide which is stable in water systems, these Friedel-Crafts type metal halide catalysts including ferric chloride, zinc chloride, copper chloride, etc. Example of phosphoric acids which may be utilized in the catalyst system of the present invention will include hypophosphoric acid, metaphosphoric acid, orthophosphoric acid, pyrophosphoric acid, polyphosphoric acid, etc. The reaction conditions under which the process of the present invention is effected will include temperatures ranging from about 50° up to about 250° C. or more and pressures ranging from atmospheric to about 100 atmospheres or more. In the preferred embodiment of the invention the reaction is effected at atmospheric pressure and at the reflux temperature of the benzene. However, if higher temperatures are desired, the reaction may be effected at superatmospheric pressures in a range hereinbefore set forth, the superatmospheric pressure being afforded by the introduction of an inert gas such as nitrogen, helium, argon, etc., in an amount so that a major portion of the reactants are maintained in the liquid phase. Generally speaking, the reaction is effected in the presence of an excess of benzene, said benzene being present in an amount in the range of from about 2:1 up to about 15:1 wt. % of benzene per wt. % of dibenzyl ether. In addition, another operating parameter is the amount of catalyst system which is present in the reaction mixture. The catalyst system will generally be present in an amount in the range of from about 0.1:1 up to about 1:1 wt. % of catalyst system per wt. % of dibenzyl ether. Examples of protonic acid catalyst systems which may be used in the present invention will include polyphosphoric acid, mixtures of polyphosphoric acid and sulfuric acid, metaphosphoric acid and sulfuric acid, orthophosphoric acid and sulfuric acid, pyrophosphoric acid and sulfuric acid, polyphosphoric acid and ferric chloride, polyphosphoric acid and zinc chloride, polyphosphoric acid and copper chloride, hypophosphoric acid and ferric chloride, hypophosphoric acid and zinc chloride, hypophosphoric acid and copper chloride.

The process of the present invention in which dibenzyl ether is reacted with benzene to synthesize diphenylmethane may be effected in any suitable manner and may comprise either a batch or continous type operation. For example, when a batch type operation is used, a quantity of benzene and the catalyst system of the type hereinbefore set forth in greater detail are placed in an appropriate apparatus. For example, when atmospheric pressure conditions are to be employed, the apparatus may comprise a reaction flask which is provided with heating and reflux means including a Dean Stark water trap whereby the water which is formed during the reaction is continously removed therefrom. The benzene and catalyst system are then heated to the desired operating temperature which, in the preferred embodiment of the invention is the reflux temperature of benzene and thereafter the benzyl ether is added thereto at a slow rate of addition. The rate of addition of the dibenzyl ether should be such that the rate of the reaction is comparable to the rate of addition. By employing an azeotropic distillation, the water, as hereinbefore set forth, is continously removed thereby insuring a relatively high conversion of the dibenzyl ether with a selectivity to diphenylmethane of greater than 90%. While the benzene is present in the reaction mixture in an excess over the dibenzyl ether, it has been found that by utilizing an excess of benzene in the upper limits of the range hereinbefore set forth it is possible to obtain selectivities of diphenylmethane of up to 96%. Upon completion of the desired residence time which may range from about 0.5 up to about 10 hours or more in duration, heating is discontinued and the reaction product is recovered from the flask. The reaction product is then recovered by conventional means of separation including washing, drying, fractional distillation, etc., whereby the diphenylmethane is separated from any unreacted dibenzyl ether and benzene as well as from the catalyst system which has been employed in the reaction. It is also contemplated within the scope of this invention that the batch type reaction may be effected at superatmospheric pressures. When this type of operation is employed, the benzene and catalyst system are placed in an appropriate pressure-resistant apparatus such as an autoclave of the rotating or mixing type. The autoclave is sealed and a substantially inert gas is placed in until the initial operating pressure has been reached. Following this, the autoclave is heated to the desired operating temperature and the dibenzyl ether is charged thereto. Upon completion of the desired residence time, heating is discontinued, the autoclave is allowed to return to room temperature and the excess pressure is discharged. The autoclave is opened, the reaction mixture is recovered therefrom and again subjected to conventional means of separation whereby the desired product comprising diphenylmethane is separated and recovered.

Another type of operation which may be employed in the synthesis of diphenylmethane comprises a continuous method of operation. When this method of operation is used, the starting materials comprising benzene and dibenzyl ether are continously charged to a reaction zone which is maintained at the proper operating conditions of temperature and pressure, said operating zone also containing a catalyst system of the type hereinbefore set forth. The dibenzyl ether and benzene are charged to the reactor at a predetermined rate, said rate being that which is sufficient to maintain an excess of benzene in the reaction zone. Upon completion of the desired residence time, the reactor effluent is continously withdrawn and again subjected to conventional means of separation whereby diphenylmethane is separated and recovered while any unreacted starting materials comprising benzene, dibenzyl ether and the catalyst system are separated from the water of reaction which is formed and returned to the reaction zone to form a portion of the feed stock.

The following examples are given for the purposes of illustrating the process of the present invention in which dibenzyl ether and benzene are reacted to synthesize diphenylmethane. However, it is to be understood that these examples are given merely for purposes of illustration and that the present invention is not necessarily limited thereto.

EXAMPLE I

A mixture comprising 93 grams (1.2 mole) of benzene along with 28 grams of polyphosphoric acid was placed in a reaction vessel provided with heating means and a Bidwell apparatus. The mixture was heated to reflux (76° C.) and thereafter a solution comprising 39.6 grams (0.2 mole) of dibenzyl ether and 10 grams of p-dichlorobenzene which was present as an internal standard were added dropwise during a period of 1 hour. The water of reaction which formed was continuously removed by means of the Bidwell reflux apparatus while the benzene was returned to the flask. At the end of 1.5 hours all of the water which had formed had been removed and no additional water was formed. The reaction mixture was refluxed for an additional period of 1 hour, at the end of which time the mixture was recovered and subjected to gas-liquid chromatographic anaylsis. The analysis was performed under conditions which included a temperature range of from 70°-240° C. at a rate of 30° C. per minute. This analysis showed a 95% conversion of the dibenzyl ether at a 78% selectivity to the desired product comprising diphenylmethane. The organic layer was separated and subjected to vacuum distillation which confirmed the yield which had been measured by the gas-liquid chromatographic analysis. The acid layer was upgraded to polyphosphoric acid by the addition of phosphorus pentoxide and utilized as the catalyst system in the next batch run.

Example II

In this example a mixture of 93 grams (1.2 mole) of benzene and 30 grams of a catalyst system comprising a mixture of polyphosphoric acid and sulfuric acid is placed in an apparatus provided with heating means and a Bidwell apparatus for collecting and removing the water of reaction. The apparatus is heated to reflux and a solution of 19.8 grams (0.1 mole) of dibenzyl ether is added dropwise to the refluxing solution during a period of 0.5 hours. The water of reaction which is formed during this time is continuously removed and the solution is maintained at reflux for an additional period of 3 hours. At the end of the 3-hour period, heating is discontinued and the reaction mixture is recovered. Gas-liquid chromatographic analysis of the product will show that a major portion of the dibenzyl ether will have been converted to diphenylmethane with a selectivity approximately the same magnitude as shown in Example I.

EXAMPLE III

In a manner similar to that set forth in the above examples, diphenylmethane is synthesized by treating 1 mole of benzene and 10 grams of a protonic acid catalyst system comprising a mixture of orthophosphoric acid and sulfuric acid with 0.1 mole of dibenzyl ether, the latter being added to a refluxing solution of the benzene and catalyst during a period of 0.5 hours. At the end of the addition period, the reaction mixture is maintained at reflux for an additional 1.5 hours. The reaction mixture which is recovered at the end of this period is subjected to gas-liquid chromatographic analysis and it will be found that a major portion of the dibenzyl ether has been converted with an almost quantitative selectivity, to the desired product, namely, diphenylmethane.

EXAMPLE IV

In this example 1.5 moles of benzene and 30 grams of a protonic acid catalyst system comprising a mixture of polyphosphoric acid and ferric chloride are placed in an apparatus provided with heating and refluxing means. The solution is heated to reflux (about 76° C.) and maintained thereat while 0.15 mole of dibenzyl ether is added dropwise during a period of 1 hour. Upon completion of the addition of the dibenzyl ether, the solution is maintained at reflux for an additional period of 1 hour, after which heating is discontinued. The reaction mixture is recovered and subjected to gas-liquid chromatographic analysis which will disclose the presence of the desired product, namely, diphenylmethane in an amount which indicates that there has been a major portion of the dibenzyl ether converted with a relatively great selectivity to the desired product.

When the above experiment is repeated utilizing a protonic acid catalyst system comprising a mixture of polyphosphoric acid and zinc chloride, it will be found that the desired product comprising diphenylmethane will be recovered in like amount.

I claim as my invention:

1. A process for the preparation of diphenylmethane which comprises reacting dibenzyl ether with benzene at a temperature of from about 50° to about 250° C. and a pressure of from about atmospheric to about 100 atmospheres in the presence of a catalytic amount of a phosphoric acid selected from the group consisting of polyphosphoric, metaphosphoric, orthophosphoric, pyrophosphoric and hypophosphoric acids, said phosphoric acid catalyst admixed with sulfuric acid.

2. The process as set forth in claim 1 in which said phosphoric acid is in an amount of from about 0.1:1 to about 1:1 weight percent acid per weight percent of dibenzyl ether.

3. The process as set forth in claim 1 in which said phosphoric acid is polyphosphoric acid.

4. The process as set forth in claim 2 in which said phosphoric acid is polyphosphoric acid.

5. The process as set forth in claim 2 in which said phosphoric acid is orthophosphoric acid.

* * * * *